United States Patent [19]
Keller

[11] 4,435,854
[45] Mar. 13, 1984

[54] HIP JOINT PROSTHESIS WITH A SHAFT TO BE FITTED INTO THE MEDULLARY CANAL OF THE FEMUR

[75] Inventor: Arnold Keller, Kaihude, Fed. Rep. of Germany

[73] Assignee: Waldemar Link GmbH & Co., Hammberg, Fed. Rep. of Germany

[21] Appl. No.: 247,776

[22] Filed: Mar. 26, 1981

[30] Foreign Application Priority Data

Apr. 24, 1980 [DE] Fed. Rep. of Germany ......... 3015690

[51] Int. Cl.³ .............................................. A61F 1/04
[52] U.S. Cl. .................................... 3/1.913; 128/92 C
[58] Field of Search ....................... 3/1.9, 1.91, 1.911, 3/1.912, 1.913; 128/92 C, 92 CA, 92 BC

[56] References Cited

U.S. PATENT DOCUMENTS 3,102,536  9/1963  Rose et al. ...................... 128/92 CA
4,135,507  1/1979  Harris ............................. 128/92 BC

FOREIGN PATENT DOCUMENTS 1030145  5/1966  United Kingdom .............. 128/92 C
1126961  9/1968  United Kingdom .............. 128/92 C
1285460  8/1972  United Kingdom .................. 3/1.91

Primary Examiner—Richard J. Apley
Assistant Examiner—D. J. Isabella
Attorney, Agent, or Firm—Prutsman, Kalb, Chilton & Alix

[57] ABSTRACT

A hip joint prosthetic device having a support shank to be fitted into the medullary canal of the femur and which, in its proximal region, has a curvature in the AP plane with a center of curvature at its anterior that makes the shank more compatible to naturally existing conditions of the femur, permits a substantial increase in the shank thickness, reduces shank tendency to turn within the medullary canal, simplifies the prosthesis operating procedures and improves the association of the shank with the trochanter region of the femur.

2 Claims, 2 Drawing Figures

HIP JOINT PROSTHESIS WITH A SHAFT TO BE FITTED INTO THE MEDULLARY CANAL OF THE FEMUR

DESCRIPTION

1. Technical Field

The present invention relates generally to a hip joint prosthetic device and more particularly to such a prosthetic device having a supporting shaft shank curved in the AP plane to be fitted into a medullary canal of the femur. In this context, the AP (anterior-posterior) plane is the plane which runs from the anterior to the posterior in the direction of the bone or shaft and is vertical to the LM (lateral-medial) plane which is parallel to the femur and intersects its knee condyles at a tangent.

2. Background Art

A hip joint prosthetic device of the type described has been disclosed in which its shank has a curvature in the AP plane with a center of curvature at its posterior. Fitting the prosthetic device shank to the curvature of the medullary canal of the femur and making the shank thicker and thus stronger, without extensive weakening of the bone, are facilitated by this means. In such a known shank design, substantial importance has been attached to providing a uniform curvature along the entire length of the shank so that it can be fitted easily into the bone cavity.

However, it has been found that a shank shape of that design requires relatively extensive milling out of the spongiosa of the femur in the region of the lesser trochanter, and that is undesirable. Moreover, such a shank design sometimes has the tendency to turn slightly in the medullary canal of the femur before the cement hardens, because the medullary canal is curved not only in the AP plane but also in the LM plane and, therefore, depending on how pronounced the curvature of the medullary canal is in the individual case, it is possible for the curved shank to more closely correspond with the shape of the canal when the curved shank is in an angular position deviating from the intended angular position. That tendency is less pronounced with shanks which are straight in the AP plane and which have therefore been preferred in practice hitherto. In comparison, the described curved shank design requires greater attention during the prosthesis operation to ensure that it remains in the proper angular position.

DISCLOSURE OF INVENTION

A principal object of the present invention, therefore, is to provide a hip joint prosthetic device of the type described which provides for fitting the shank to the naturally existing conditions of the medullary canal of the femur, and which as a result has a substantial shank thickness, has a reduced tendency to turn during installation and therefore presents fewer demands on the operating technique and provides an advantageous shank cross-section and force distribution in the trochanter region.

The solution according to the present invention consists in forming the shank, in its proximal region, with a curved section having a curvature in the AP plane with a center of curvature in the AP plane anterior of the shank and preferably with the curved section extending a distance between about 4–8 cm in the AP plane from an end flange which constitutes the proximal termination of the shank. The change in the direction of the shank which is provided by the curvature in the AP plane is appropriately in the range of about 5°–10°. The distal region of the shank can be straight or, preferably, of opposite curvature in the AP plane (with its center of curvature at the posterior of the shank). Any desired curvature of the shank in the LM plane remains unaffected by the invention.

It has been found that a prosthetic device made in accordance with the present invention in general does not have a substantial tendency to turn relative to its intended angular position. As a result, the operating technique is simplified. Fitting the shank to the naturally existing conditions of the femur is improved and is very good. In particular, the shank curvature according to the present invention provides for advantageously positioning the shank in the trochanter region. The osseous tissue in the region of the lesser trochanter is protected without requiring the cavity preparation on the opposite side for receiving the shank approaching too closely to the cortical substance or even weakening that substance. Excellent prosthesis strength in the trochanter region of the bone is achieved, because as seen in FIG. 1 the direction of the axis of the shank of the prosthetic device at its proximal end is approximately the same as or identical to the direction of the axis of the neck leading to the head of the prosthetic device. Any suspicion or fear that, because of the change in the curvature of the shank, its introduction into the medullary canal would not be possible or would be possible only with damage, have not been confirmed.

Other objects will be in part obvious and in part pointed out more in detail hereinafter.

A better understanding of the invention will be obtained from the following detailed description and the accompanying drawing of an illustrative application of the invention.

BEST MODE FOR CARRYING OUT THE INVENTION

Figures 1, 2:
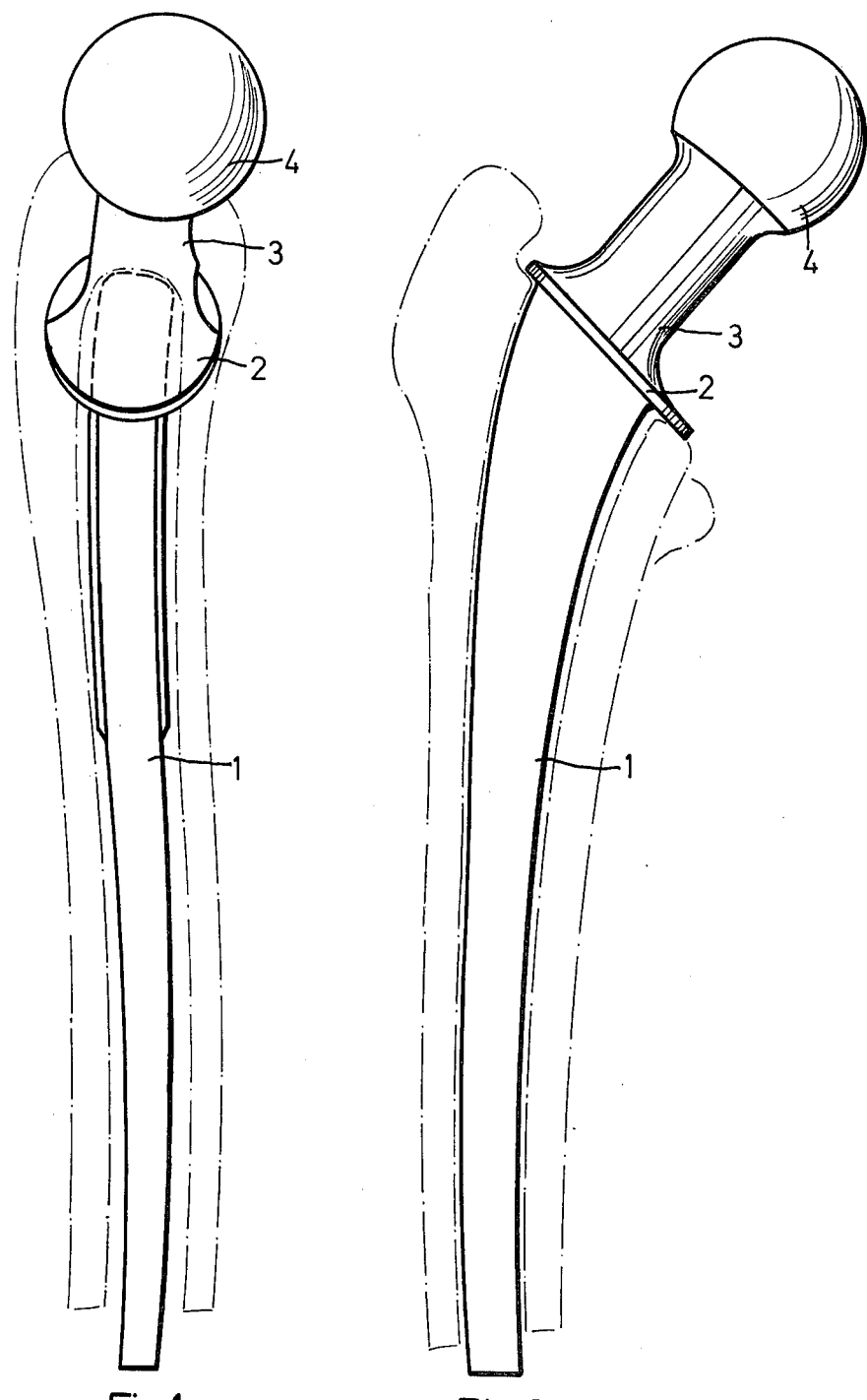
FIG. 1 is a side view (or projection onto the AP or anterior-posterior plane) as viewed from the medial direction, of a left prosthesis incorporating an embodiment of a hip joint prosthetic device of the present invention.
FIG. 2 is a side view (or projection onto the LM or lateral-medial plane) of the left prosthesis as viewed from the dorsal direction.

Referring now to the drawing in detail, a hip joint prosthetic device incorporating an embodiment of the present invention consists of a shank 1 having an end flange 2 which constitutes the proximal termination of the shank, a head 4 providing a ball for a hip socket and a narrow elongated neck 3 for connecting the head 4 to the shank 1. In a projection onto the LM or lateral-medial plane as seen in FIG. 2, the shank 1 is curved in a direction so that the increased lateral width or dimension of the shank 1 in the LM plane projection from its distal end to its proximal end compensates for the increase in curvature of the shank in such a way that the shank can be introduced easily into the medullary canal of the femur, the section of which is indicated by broken lines in both FIGS. 1 and 2.

The features of the shank 1 according to the present invention are shown in FIG. 1, from which it can be seen that the shank has a S-shaped curvature in the AP or anterior-posterior plane. As viewed in FIG. 1, and with regard to the front or anterior of the shank 1, the shank 1 is slightly concave in the proximal region and slightly convex in the distal region. The decrease in the lateral width or dimension of the shank in the AP plane from its top to its bottom is relatively slight. It can be seen that the S-shaped curvature of the shank 1 in the AP plane is very well suited to the curvature of the medullary canal in the central and distal regions. Furthermore, it can be seen that a good fit is also achieved in the proximal region by a corresponding shape of the cavity formed in the spongiosa, more osseous material remaining on the dorsal side of the trochanter region (at the left as viewed in FIG. 1) than on the ventral side (at the right as viewed in FIG. 1), although the individual conditions and the course of the operation may cause deviations in that respect. The region of the lesser trochanter is protected in that manner.

As can be seen in FIG. 1, there is an anteversion of the head 4 which is manifested by a slight inclination of the neck 3 toward the head 4 to the right as viewed in FIG. 1, as compared with the overall longitudinal axis of the prosthetic device. Thus, according to the present invention, the shank curvature of the proximal part of the shank provides for shifting the shank into general alignment (in the AP plane as viewed in FIG. 1) with the neck 3. Such contributes to harmonious stress distribution within the prosthesis and effective transfer of force to the bone, especially at its proximal end.

As will be apparent to persons skilled in the art, various modifications, adaptations and variations of the foregoing specific disclosure can be made without departing from the teachings of the present invention.

I claim:

1. In a hip joint prosthetic device comprising a rigid shank to be fitted into the medullary canal of the femur, a head, a end flange at the proximal end of the shank, a head and a neck section extending from the end flange to the head, the head being anteverted relative to the shank in the LM (lateral-medial) plane, the improvement wherein the shank has, in the proximal region thereof, a section extending a distance between approximately 4-8 cm from the end flange which is curved in the AP (anterior-posterior) plane with a center of curvature in the AP plane anterior of the proximal region of the shank, wherein the axis of the shank at its proximal end extends, in the AP plane, approximately in the direction of the longitudinal axis of the neck section and wherein the shank has, in the distal region thereof, a section curved in the AP plane in the opposite direction to said proximal section.

2. A hip joint prosthetic device according to claim 1 wherein the axis of said curved section of shank has an angular change in direction in the AP plane of approximately 5°-10°.

* * * * *